(12) United States Patent
Couves et al.

(10) Patent No.: US 6,407,283 B2
(45) Date of Patent: Jun. 18, 2002

(54) PROCESS FOR THE PRODUCTION OF VINYL ACETATE

(75) Inventors: John William Couves, High Wycombe; Simon James Kitchen, Doncaster, both of (GB)

(73) Assignee: BP Chemicals Limited, London (GB)

( * ) Notice: Subject to any disclaimer, the term of this patent is extended or adjusted under 35 U.S.C. 154(b) by 0 days.

(21) Appl. No.: 09/894,792

(22) Filed: Jun. 28, 2001

Related U.S. Application Data

(62) Division of application No. 09/415,972, filed on Oct. 12, 1999, which is a division of application No. 08/960,306, filed on Oct. 29, 1997, now Pat. No. 5,990,344.

(51) Int. Cl.$^7$ .............................................. C07C 67/05
(52) U.S. Cl. .................................................... 560/245
(58) Field of Search ........................................ 560/245

(56) References Cited

U.S. PATENT DOCUMENTS

| | | |
|---|---|---|
| 3,847,972 A | 11/1974 | Kominami et al. |
| 4,145,314 A | 3/1979 | Fung et al. ................. 252/437 |
| 4,482,641 A | 11/1984 | Wennerberg ................ 502/182 |
| 4,777,152 A | 10/1988 | Tsukada ........................ 501/80 |
| 4,808,394 A | 2/1989 | Kolts et al. .................. 423/437 |
| 4,954,474 A | 9/1990 | Tsurmi et al. ............... 502/185 |
| 5,179,056 A | 1/1993 | Bartley ........................ 502/170 |
| 5,196,389 A | 3/1993 | Dubots ........................ 502/178 |
| 5,336,802 A | 8/1994 | Smith et al. ................. 560/245 |
| 5,429,780 A | 7/1995 | Prin et al. ...................... 264/44 |
| 5,468,370 A | 11/1995 | Ledoux et al. .............. 208/134 |
| 5,990,344 A | * 11/1999 | Couves et al. .............. 560/245 |

FOREIGN PATENT DOCUMENTS

| | | |
|---|---|---|
| EP | 685451 | 12/1995 |
| EP | 0723810 A1 | 7/1996 |
| EP | 723810 | 7/1996 |
| WO | WO 97/26988 | 7/1997 |

OTHER PUBLICATIONS

*Activation, Deactivation and Poisoning of Catalysts*, pp. 16–17, Butt, John A, Academic Press (1988).

* cited by examiner

*Primary Examiner*—Paul J. Killos
*Assistant Examiner*—Zachary Tucker
(74) *Attorney, Agent, or Firm*—Fay, Sharpe, Fagan, Minnich & McKee, LLP

(57) ABSTRACT

A process for the production of vinyl acetate which comprises contacting ethylene, acetic acid and an oxygen-containing gas with a supported palladium catalyst prepared by a process comprising the steps of (a) impregnating a catalyst support with a palladium compound, (b) converting the palladium compound to substantially metallic palladium, and (c) sintering the supported palladium at a temperature of greater than 500° C.

11 Claims, 3 Drawing Sheets

PROCESS FOR THE PRODUCTION OF VINYL ACETATE

This application is a division of application Ser. No. 09/415,972, filed Oct. 12, 1999, which is a division of application Ser. No. 08/960,306, filed Oct. 29, 1997, now U.S. Pat. No. 5,990,344.

The present invention relates to a process for the production of vinyl acetate by contacting ethylene, acetic acid and an oxygen-containing gas with a supported palladium catalyst.

The preparation of supported palladium catalysts for the production of vinyl acetate generally involves impregnating a suitable support with a palladium compound followed by conversion of the palladium compound to substantially metallic palladium.

Methods for the preparation of shell-impregnated catalysts are described, for example, in U.S. Pat. No. 3,822,308, U.S. Pat. No. 4,048,096, U.S. Pat. No. 5,185,308, U.S. Pat. No. 5,332,710, CA 2128162, U.S. Pat. No. 4,087,622, CA 2128154, CA 2128161 and U.S. Pat. No. 5,422,329.

Methods for the preparation of non-shell type catalysts are described in, for example, U.S. Pat. No. 3,743,607, GB 1333449, U.S. Pat. No. 3,939,199, U.S. Pat. No. 4,668,819, EP 330853, EP 403950, EP 431478 and CA 2071698.

U.S. Pat. No. 5,336,802 describes a method for the pre-treatment of palladium-gold catalysts in which the catalyst is heated in the presence of an oxidising agent such as air at a temperature at least sufficient to partially oxidise the palladium; the oxidising agent is withdrawn and an inert gas such as nitrogen is introduced; the catalyst is then heated again at a temperature up to 500° C. in the presence of a reducing agent such as hydrogen or ethylene. The process described therein is illustrated with a "conventional catalyst containing nominally 1% palladium and 0.5% gold".

It is known that the activity for vinyl acetate production of supported palladium catalysts declines with use If the catalyst's activity and hence the process productivity declines to a commercially unacceptable level, it is necessary to regenerate and/or replace the catalyst. Deactivation of vinyl acetate catalysts is described by Abel et al. in Chem. Eng. Technol. 17 (1994) 112–118.

Merely increasing the amount of palladium in the catalyst to increase the lifetime of the catalyst presents a problem in that the initial activity of the catalyst may be too high for safe and/or controllable operation on an industrial scale, for example, due to the limited heat removal capacity of the plant.

There remains a need for a process for the preparation of a supported palladium catalyst for use in the production of vinyl acetate which overcomes this problem.

Thus, according to the present invention, there is provided a process for the production of vinyl acetate which process comprises contacting ethylene, acetic acid and an oxygen-containing gas with a supported palladium catalyst prepared by a process comprising the steps: (a) impregnating a catalyst support with a palladium compound, (b) converting the palladium compound to substantially metallic palladium, and (c) sintering the supported palladium at a temperature of greater than 500° C.

The present invention solves the technical problem defined above by sintering the palladium on the support at a temperature of greater than 500° C.

Without wishing to be bound by any theory it is believed that this sintering step causes palladium metal particle growth which decreases the initial activity of the catalyst. Thus, catalysts having, a high palladium concentration but a commercially acceptable initial activity may be prepared by the process according to the present invention and such catalysts have a longer commercially useful life than conventional catalysts. The sintering step also increases the average pore size of silica supports. The catalysts of the present invention have also been found to be less susceptible to the adverse effects of excess concentration of promoter such as potassium acetate.

The sintering step (c) is preferably performed using a reducing gas, but can be performed in the presence of an oxidising gas or in an inert gas. Suitable reducing gases are hydrogen and carbon monoxide. A suitable oxidising gas is oxygen. These may be diluted with an inert gas Suitable inert gases for use alone or in conjunction with oxidising, or reducing gases are nitrogen, carbon dioxide and helium. Suitable temperatures for the sintering step are from greater than 500 to 1000° C. with preferred temperatures being in the range 650–1000° C. Preferred times for the sintering step are between 1 and 24 hours. If an oxidising gas is used then the catalyst needs to be subsequently reduced. The catalyst can be purged with an inert gas prior to sintering and during the heat-up period (for safety) and during cool-down (to less than 100° C., more preferably to less than 60° C.) to prevent any redispersion of the palladium. Any suitable or practicable heat-up and cool-down rates can be used. The sintering step (c) on a commercial scale can be performed in a tower or vessel capable of fulfilling the process conditions outlined above. The catalyst can be agitated by the gas flow during the process. A rotary screw furnace can be used On the laboratory scale, a horizontal or vertically mounted tube in an electric furnace can be used provided that gas-solid contact is efficient (length/diameter will need to be considered). Pre-heating of the gas stream may be required. The time and temperature of the sintering step are related; the higher the temperature, the shorter the time required. Those skilled in the art will be able to adapt these parameters to fit the scale of operations. Typically the sintering step (c) causes palladium metal particle growth from 3–4 nm in diameter to 8–15 nm in diameter.

The conversion of the palladium compound to substantially metallic palladium in step (b) may be achieved by a reduction step which can immediately precede the sintering step (c) and by performing the two process steps in the same equipment.

The catalyst preparation process of the present invention may be used for the preparation of uniformly impregnated or shell impregnated catalysts, for use in fluid bed or fixed bed processes for the production of vinyl acetate.

The catalyst preparation process of the present invention may be used to prepare catalysts having high palladium concentrations, for example greater than 0.5% by weight, preferably greater than 1% by weight based upon the total weight of the catalyst. The palladium concentration may be as high as 5% by weight for fluid bed or as high as 10% by weight for fixed bed applications. The initial activity of a supported palladium catalyst having high palladium concentration, if prepared by a conventional process, would be expected to be very high and might even be so high as to be unsafe and/or uncontrollable if used on a commercial scale. However, when prepared by the process of the present invention, the initial activity of the catalyst is reduced compared to that of a conventionally prepared catalyst, whereas the high palladium concentration results in commercially acceptable activity for the extended lifetime of the catalyst.

For the preparation of both shell impregnated and uniformly impregnated catalysts, suitable catalyst supports may comprise porous silica, alumina, silica/alumina, titania, zirconia or carbon, preferably silica. Suitably, the support may have a pore volume from 0.2 to 3.5 ml per gram of support, a surface area of 5 to 800 m² per gram of support and an apparent bulk density of 0.3 to 1.5 g/ml. For catalysts used in fixed bed processes the support typically has dimensions of 3 to 9 mm. For catalysts used in fixed bed processes the support typically may be spheric, tablet, extrudate, pill shaped or any suitable shape. For catalysts used in fluid bed processes the support typically may have a particle size distribution such that at least 60% of the catalyst particles have a particle diameter of below 200 microns, preferably at least 50% less than 10 microns and no more than 40% of the catalyst particles have a diameter less than 40 microns.

In step (a) the support is preferably impregnated with a palladium compound in a suitable solvent Suitable solvents may be water, carboxylic acids such as acetic acid, benzene, toluene, alcohols such as methanol or ethanol, nitriles such as acetonitrile or benzonitrile, tetrahydrofuran or chlorinated solvents such as dichloromethane. Preferably, the solvent is water and/or acetic acid. Suitably, the support is impregnated with palladium acetate, sulphate, nitrate, chloride or halogen-containing palladium salts such as $H_2PdCl_4$, $Na_2PdCl_4$ or $K_2PdCl_4$. A preferred water soluble compound is $Na_2PdCl_4$ A preferred acetic acid-soluble palladium compound is palladium acetate.

The impregnation of the support may be performed by dipping, immersion or spraying the support in contact with a solution of the palladium compound. The impregnation may be performed in one or more steps or in a continuous process. The support may be contacted with the impregnating palladium solution by tumbling, rotating, swirling or a similar process, to give uniform impregnation. The impregnation is typically performed at ambient temperature. Elevated temperatures may be used for example, with palladium acetate in acetic acid, up to 120° C., preferably up to 100° C., more preferably up to 60° C. Impregnation is performed carefully so as to avoid the break up or attrition of the support. The support can be filled up by the impregnating solution to 5–100% of the pore volume.

In addition to palladium compounds the support may also be impregnated in step (a) with gold, copper and/or nickel compounds, preferably gold, which are converted to the metal along with the palladium in step (b) and are present as mixtures and/or alloys with the palladium in the metallic palladium particles. Suitable gold compounds include gold chloride, tetrachloroauric acid ($HAuCl_4$), $NaAuCl_4$, $KAuCl_4$, dimethyl gold acetate, barium acetoaurate or gold acetate, preferably $HAuCl_4$. These promoters may be used in an amount of 0.1 to 10% by weight of each promoter metal present in the finished catalyst.

In addition to palladium and optional gold, copper and/or nickel the support may also be impregnated at any suitable stage during the preparation process with one or more salts of Group I, Group II, lanthanide or transition metals, preferably of cadmium, barium, potassium, sodium, iron, manganese, nickel, antimony and/or lanthanum, which are present in the finished catalyst as salts, typically acetates. Generally potassium will be present. Suitable salts of these compounds are acetates or chlorides but any soluble salt may be used. These promoters may be used in an amount of 0.1 to 15%, preferably 3 to 9%, by weight of each promoter salt present in the finished catalyst.

The impregnated support may optionally be dried and the impregnation step repeated two or more times if higher palladium or promoter loadings, than the solubility of the salt in the solvent will allow, are required. The drying step may be performed at up to 120° C., preferably up to 100° C., and most preferably at 60° C. The drying step may be performed at ambient temperature and reduced pressure. Air, nitrogen, helium, carbon dioxide or any suitable inert gas may be used in the drying step. The catalyst may be tumbled, rotated or agitated by the gas stream to aid drying.

To prepare shell impregnated catalysts the wet or dry impregnated support is contacted with a base solution with swirling, tumbling, rotation, mixing or the like. The base solution can also be applied by spraying onto the impregnated support during tumbling, rotation, mixing or the like. Bases can be Group I or II hydroxides, carbonates or silicates. Typical examples are sodium hydroxide, sodium metasilicate, potassium hydroxide, potassium metasilicate and barium hydroxide. The base solution can be applied in one or more steps with suitable time delays between applications. The temperature of the precipitation step is usually ambient but can be raised up to 100° C. Any solvent can be used in which the base material is soluble, water is preferred. The base should be contacted with the impregnated support for a suitable period so that the metal salts are precipitated in a shell. This usually takes greater than one hour, preferably between 8 to 24 hours. An optimal amount of base will be required for the precipitation and is usually required in excess, commonly this is 1.8 times the notional amount required to generate the hydroxides of the metal salts.

The impregnated support can be washed to remove anion contaminants, for example, nitrates, sulphates and usually halides. For chloride removal, washing with de-ionised water should proceed until a silver nitrate test shows that there is no chloride present. The anion contamination levels should be minimised. Cation contaminants should be minimised; for example to below 0.5 wt %, preferably below 0.2 wt % of sodium in the dried catalyst. Low levels of these contaminants are likely to remain; it is not essential that the levels are absolutely zero. On a commercial scale, batch washing may be used. To speed up the process, warm water may be used. Also, ion exchange solutions (such as potassium acetate) can be used to displace chloride and sodium. Also, the reagents used for the preparation can be selected to avoid the use of chloride and sodium, for example, potassium metasilicate instead of a sodium salt.

In step (b) the palladium compound can be converted to metal before or after the optional washing step above, depending on the reagents used. Liquid reducing agents such as aqueous hydrazine, formaldehyde, sodium formate, methanol or alcohols, preferably aqueous hydrazine can be used. Reduction may also be performed with gases such as carbon monoxide, hydrogen and ethylene. These can be diluted with an inert gas such as nitrogen, carbon dioxide or helium. Typically, the gaseous reduction takes place at elevated temperatures of 100–500° C. until the material is reduced. Typically, reduction in the liquid reducing agents takes place and ambient temperatures but temperatures up to 100° C. may be used.

After the palladium has been converted to metal it is sintered as herein described. The sintering step (c) may follow on from the step (b) by further heating the catalyst in the reducing gas to greater than 500° C. The material may then be impregnated with promoter salts as herebefore described.

The ethylene, acetic acid and oxygen-containing gas may be contacted with the supported palladium catalyst prepared according to the catalyst preparation process of the present invention by methods known in the art. Thus, the reactants may be contacted with the catalyst in a fixed bed or a fluid bed at temperatures in the range 145 to 195° C. and pressures in the range 1 atm to 20 atm. The vinyl acetate product may be recovered by conventional methods known in the art.

The invention will now be illustrated by reference to FIGS. 1 to 3 and the following examples and experiments. FIG. 1 is a schematic representation of some of the possible catalyst preparation methods according to the present invention.

Figure 1:
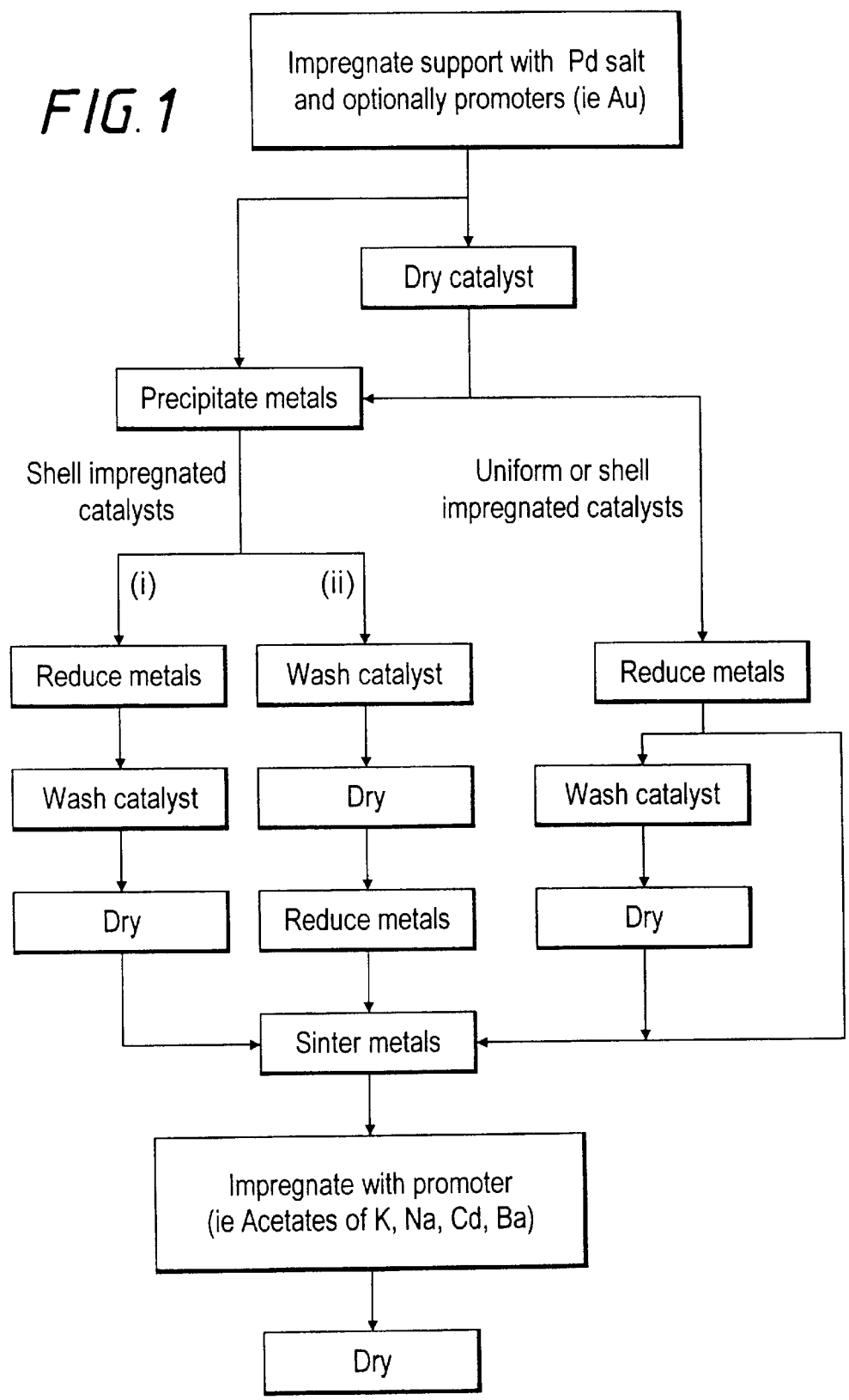

Referring to FIG. 1 uniform (non-shell) type catalysts may be prepared by the steps of impregnating a support with palladium salts and optional promoters followed by drying and reduction of the metals. The material may then be optionally washed and dried before sintering according to the present invention and final impregnation with optional promoters such as acetates of potassium, sodium, cadmium or barium To prepare shell type catalysts the support impregnated with palladium and optional promoters such as gold may be optionally dried. The metals are then precipitated. The material may then be passed to either (i) reduction to metals, washing and drying, or (ii) washing and drying followed by reduction to metals. The material is then subjected to sintering according to the present invention followed by impregnation with promoters such as acetates of potassium, sodium, cadmium or barium.

EXAMPLE 1

Catalyst A was prepared according to the present invention to have a notional composition (that is without allowing for any losses during preparation) of 1.8% by weight palladium, 0.8% by weight gold and 7% by weight potassium acetate.

1. Impregnation of support 15 g of KA160 silica support spheres (4–6 mm, SudChemie) were added to a solution of 1.0264 g of sodium tetrachloropalladate trihydrate (Johnson Matthey) and 0.2655 g of chloroauric acid trihydrate (Aldrich) in 9.1 g of de-ionised water. The addition was done in one portion and the mixture swirled until all the solution had been absorbed evenly. The impregnated support was then allowed to stand covered for two hours at room temperature.

2. Precipitation of palladium and gold compounds on support

A solution of 1.7 g sodium metasilicate pentahydrate (Fisons) in 18 g of water was added to the impregnated support from step 1. The mixture was swirled briefly a few times over 15 minutes to avoid the formation of "spots" and then permitted to stand undisturbed overnight 3 Reduction of palladium and gold to substantially metallic state The aqueous phase above the material from step 2 was treated with 5 g of 55% hydrazine hydrate (Aldrich).

4. Washing of supported compounds

The aqueous phase was decanted off and the material from step 3 was washed four times with about 50 ml of water, decanting after each wash. The resultant material was transferred to a glass column fitted with a stopcock and then washed with de-ionised water at approximately 1 liter per 12 hours until a silver nitrate test proved negative. The material was dried at 60° C. overnight in a forced air oven and cooled.

5. Sintering of palladium (and gold)

The supported palladium material from step 4 was transferred to a horizontally mounted furnace and packed into the center of a quartz tube liner with quartz wool and KA160 support (previously dried thoroughly) filling the void space. The quartz tube liner was placed inside a steel tube and gas supplies connected. The furnace temperature was raised to 150° C. at 10° C./min and maintained at this temperature for 2 hours under a constant stream of nitrogen. Hydrogen flow at a GHSV of 60/hr was commissioned and the nitrogen flow stopped. The furnace temperature was raised to 800° C. at 30° C./min and maintained at this temperature for 11 hours. After this period the resultant material was allowed to cool to room temperature under hydrogen flow. Nitrogen flow was re-commenced and hydrogen flow stopped before discharging the material.

6. Metal Acetate Impregnation

The dry material from step 5 was impregnated with 1.16 g of anhydrous potassium acetate (Aldrich) dissolved in 8.8 g of water. The mixture was swirled gently until the liquid was absorbed. The resultant material was dried again overnight at 60° C.

EXAMPLE 2 (COMPARATIVE)

Catalyst B was prepared according to the procedure of Example 1 except that the sintering step 5 was omitted.

EXAMPLE 3 (COMPARATIVE)

Catalyst C was prepared according to the procedure of Example 1 except that the sintering step 5 was omitted and metal loadings were reduced to give the same initial activity as the catalyst prepared in Example 1.

Catalyst Testing in Microrector

The catalysts prepared above were tested in a microrector using the following general procedure. The tests were performed at 7.8 barg and 150° C. using catalyst pellets (prepared as above, amount specified in Table 1) diluted with 60 ml of 1 mm glass beads and loaded into a stainless steel tube of internal diameter 10–11 mm. The catalyst was commissioned at 7.8 barg by heating at 160° C. for 3 hours in a stream of nitrogen and then 150° C. in a stream of ethylene. Acetic acid vapor was then mixed with the ethylene and passed over the catalyst for a period of at least 50 minutes. A mixture of 21% oxygen in helium was gradually added to the feed gas while maintaining the maximum catalyst bed temperature at 150° C. The catalyst hot spot was maintained at 150° C. The final composition of the reactant mixture was ethylene acetic acid oxygen:helium= 53.1:10.4:7.7:28.6 by volume and the total gas hourly space velocity was 3850 hr$^{-1}$. The product stream was analysed in the vapor phase at hourly intervals by means of an on-line gas chromatograph.

Activity of the catalyst was calculated as grams of vinyl acetate produced per liter of catalyst per hour (space time yield, STY) and the selectivity of the catalyst was calculated as the percentage of converted ethylene present in the product. Data is reported on the basis of the average of the activities and selectivities measured between 17 and 22 hours after full oxygen content was achieved.

The results, comparing the activities of catalyst A, B and C, are presented in Table 1.

TABLE 1

| | Catalyst | Catalyst loaded in micro-reactor (grams) | Activity (grams of vinyl acetate per hour per liter of catalyst) | Selectivity (%) |
|---|---|---|---|---|
| Example 4 | A | 2.5 | 715 | 92.4 |
| Example 5 (comparative) | B | 2.0 | 1381 | 90.7 |
| Example 6 (comparative) | C | 2.5 | 718 | 93.4 |

A comparison of the activities of catalysts A and B in Table 1 shows that the sintering step, (step 5) caused the activity of catalyst A to be decreased. This is consistent with growth of palladium particle size and loss of palladium metal surface area. Catalyst C was prepared with lower metal loadings than catalysts A and B; the metal loadings being selected to give the same initial activity as catalyst A. Catalysts A and C would thus be expected to have similar initial operational behavior. It would however be expected that catalyst A would maintain productivity for a longer period than catalyst C if palladium particle growth and loss of palladium metal surface area are the cause of reduced initial activity. This is illustrated in Examples 7 and 8.

Testing of Catalysts in Larger Reactors

Catalysts A and C were tested in larger tubular reactors as follows. 77.5 g of catalyst A (Example 7) and 77.5 g of catalyst C (Example 8 comparative) were each loaded into separate 6 foot reactor tubes. These two tubes were placed in the same fluidised bed sand bath. The bath temperature could be controlled and each tube had its own gas/liquid feed and product handling system. Nitrogen flow was commenced at 1106 ml/min (@STP) and ethylene flow at 2590 ml/min (@STP).

Figure 2:
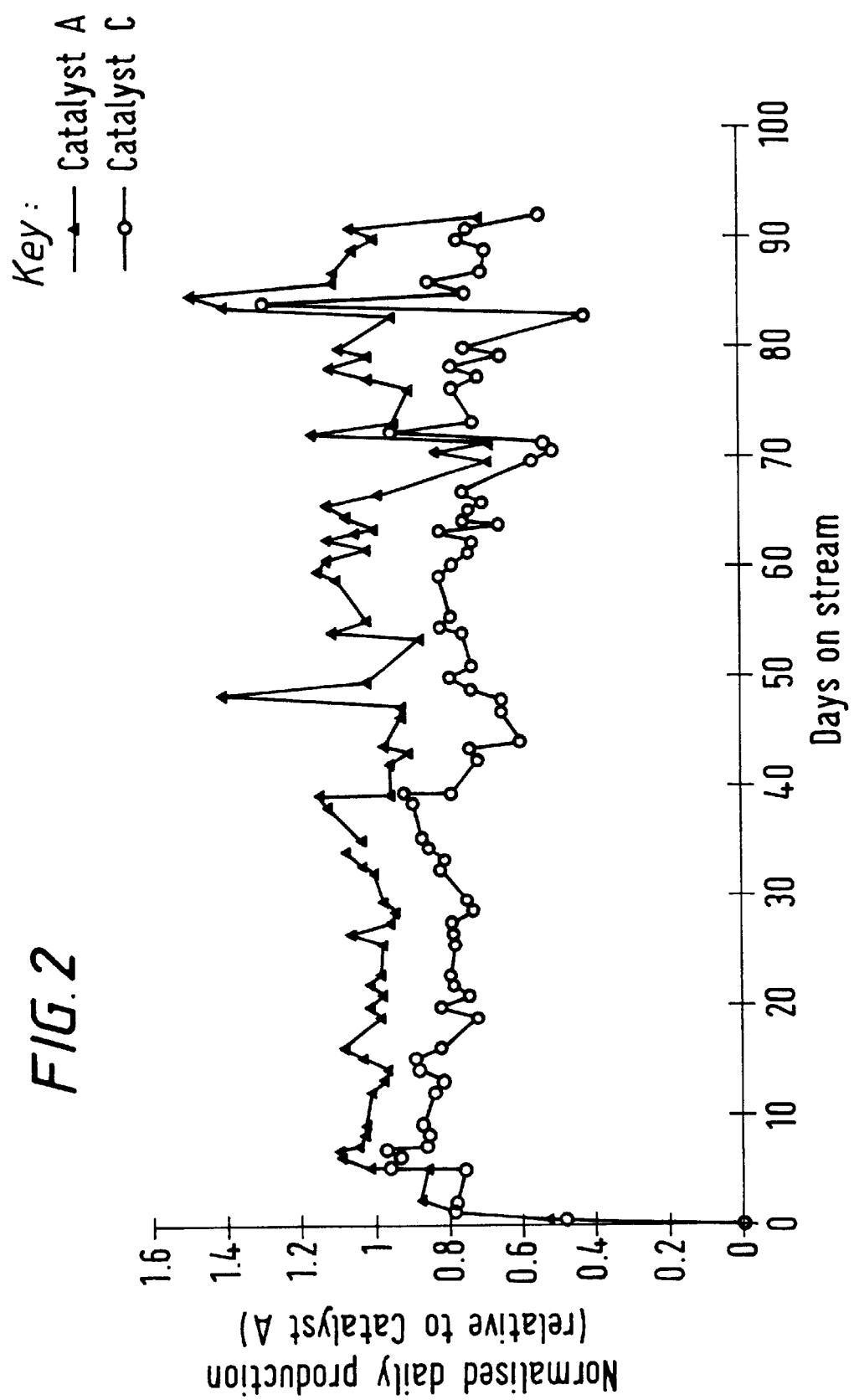
FIG. 2 is a graph comparing productivity as a function of time of a catalyst prepared according to the invention to that of a catalyst not prepared according to the invention.

The sand bath and tubes were heated to 150° C. and the reactor pressure was raised to 115 psig. Acetic acid flow at 155 g/hr (containing 2 wt % water) was commenced to a vapouriser and mixed with nitrogen and ethylene. A small stream of acetic acid (2 wt % water, 0.0285 wt % potassium acetate) at 13 g/hr was introduced to the preheater zone to be vaporised with the main gas stream. After a few hours oxygen was commenced at 153 ml/min (@STP). The product stream was analysed by on-line chromatography and then condensed to give a crude liquid product of vinyl acetate, acetic acid and water, the remaining gases were vented and sampled by the on-line gas chromatography. Vinyl acetate production was monitored for both catalysts. As the catalysts deactivated a constant production rate was initially maintained by gradually increasing the oxygen feed to a maximum level of 425 ml/min (@STP). At fully oxygen flow the gas feed composition was ethylene acetic acid water oxygen nitrogen=49.7:19.6:1.3: 8.2:21.2 by volume at a total GSHV of 2261 hr$^{-1}$ (@STP). Once full oxygen feed rate was achieved, constant production on catalyst A was further maintained by gradually increasing the sand bath temperature from approximately 150 to 160° C. Since both tubes were in the same sand bath catalyst C production fell below that of catalyst A as it deactivated more rapidly FIG. 2 shows the normalised daily production for catalysts A and C as a function of days on stream. FIG. 2 clearly demonstrates that although the initial production capability of the two catalysts was similar, after five days on stream, the productivity of the comparative catalyst, catalyst C, was below that of the catalyst of the invention, catalyst A. Examination of the slopes of the productivities of the two catalysts shows that catalyst A maintained production at approximately 1 whereas catalyst C's productivity slowly declined with time, ending up at a productivity of 0.7. Towards the end of the run the production capabilities of catalyst A were tested relative to catalyst C by adjusting the oxygen feed levels and/or sand bath temperature. The production is seen to alter upwards and downwards accordingly in FIG. 2 and it is noted that catalyst A always has a higher productivity than catalyst C. Catalyst A has exhibited a slower deactivation rate than catalyst C even though their initial activities were very similar.

EXAMPLE 9

Further Catalyst Tests Using Microreactor

Figure 3:
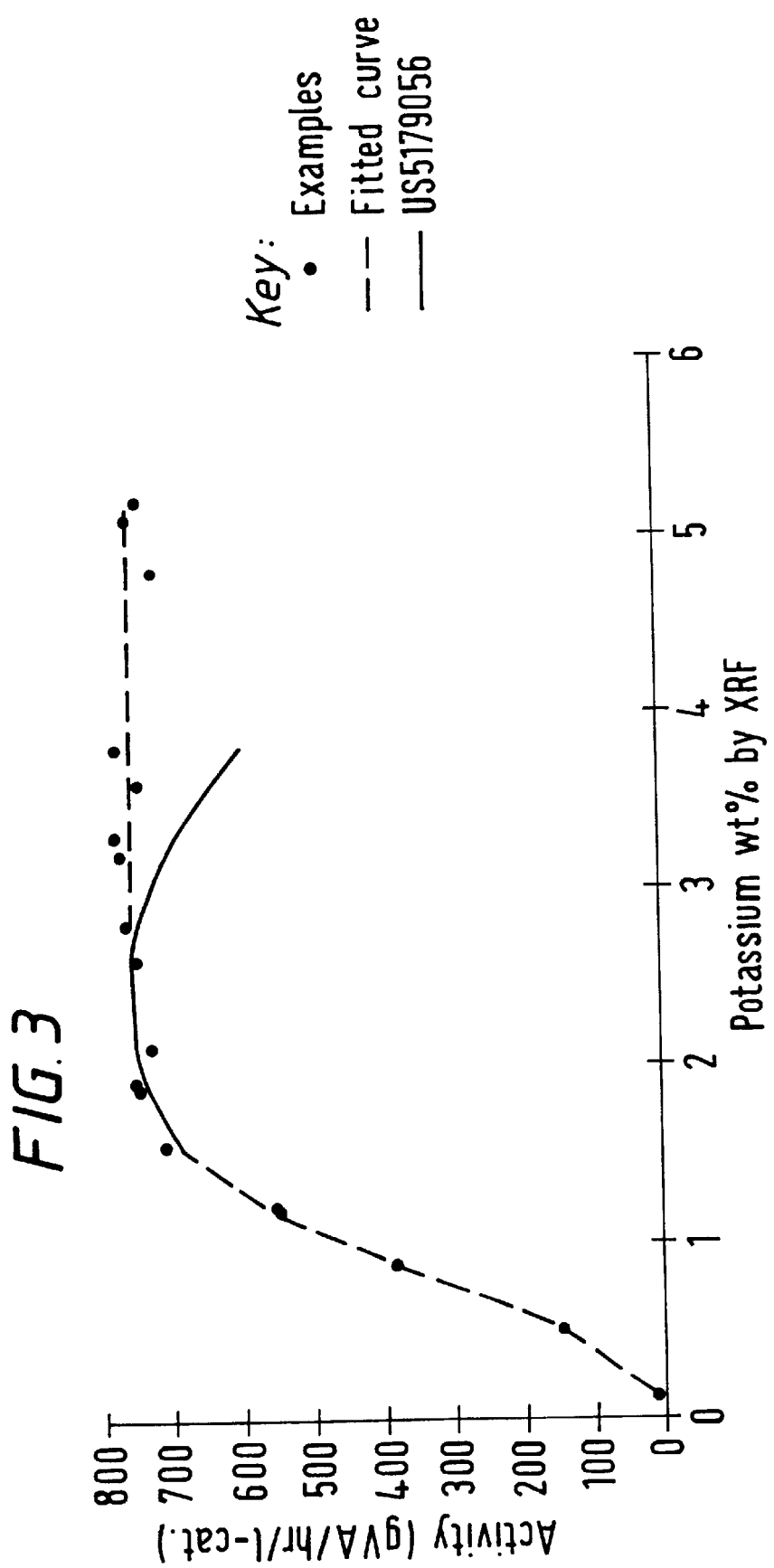
FIG. 3 is a graph comparing the effect of the amount of promoter potassium acetate has on the activity of a catalyst prepared according to the invention to that of catalysts not prepared according to the invention.

Two further batches of catalyst were prepared according to the procedure of Example 1 except that the quantities of reagents used were scaled by a factor of 9. After the washing and drying step each catalyst batch was divided accurately into 9 equal portions and impregnated with the target wt % potassium acetate loadings (see Table 2). These catalyst samples were tested according to the procedure of Examples 1 to 3. FIG. 3 shows the activity achieved by these catalyst samples and compares it to the activity of the corresponding catalysts reported in U.S. Pat. No. 5,179,056 (this activity is extrapolated according to the model described in U.S. Pat. No. 5,179,056). FIG. 3 shows that that the catalyst according to the present invention requires a minimum level of approximately 1.5 wt % potassium to be effective whereas for the catalyst of the patent U.S. Pat. No. 5,179,056, a maximum in activity was achieved at approximately 2.5 wt % potassium. For the catalyst according to the present invention, the effect of the promoter is approximately constant from approximately 1.5 to 5 wt % potassium. For the catalyst according to U.S. Pat. No. 5,179,056 activity begins to fall as promoter loadings are increased.

TABLE 2

| Target (wt. %) Potassium Acetate | Potassium (wt. %) by XRF method | Activity (g Vinyl Acetate/hr/l of catalyst) | Selectivity (%) | Activity according to model | Activity as in U.S. Pat. No. 5179056 |
|---|---|---|---|---|---|
| 0 | 0.12 | 11 | 1 | 13 | |
| 1 | 0.5 | 147 | 74.5 | 142 | |
| 2 | 0.87 | 385 | 89.1 | 382 | |
| 3 | 1.17 | 548 | 91 | 556 | |
| 3 | 1.2 | 554 | 90.3 | 570 | |
| 4 | 1.54 | 710 | 92 | 687 | 688 |
| 5 | 1.86 | 745 | 92.5 | 735 | 731 |
| 5 | 1.9 | 752 | 91.4 | 738 | 735 |
| 6 | 2.1 | 729 | 92.8 | 749 | 751 |

TABLE 2-continued

| Target (wt. %) Potassium Acetate | Potassium (wt. %) by XRF method | Activity (g Vinyl Acetate/hr/l of catalyst) | Selectivity (%) | Activity according to model | Activity as in U.S. Pat. No. 5179056 |
|---|---|---|---|---|---|
| 7 | 2.6 | 750 | 91.8 | 757 | 759 |
| 8 | 2.8 | 764 | 92.8 | 757 | 748 |
| 9 | 3.2 | 771 | 93.1 | 757 | 706 |
| 9 | 3.3 | 778 | 91.5 | 757 | 691 |
| 10 | 3.6 | 745 | 93.3 | 757 | 639 |
| 11 | 3.8 | 776 | 92.1 | 757 | 599 |
| 14 | 4.8 | 719 | 93.3 | 757 | |
| 15 | 5.1 | 759 | 93 | 757 | |
| 15 | 5.2 | 743 | 91.8 | 757 | |

This shows that the catalyst prepared according to the present invention is more tolerant of excessive potassium acetate promoter concentrations.

What is claimed is:

1. The process for the production of vinyl acetate which process comprises contacting ethylene, acetic acid and an oxygen-containing gas with a supported palladium catalyst prepared by a process comprising the steps: (a) impregnating a catalyst support with a palladium compound, (b) converting the palladium compound to substantially metallic palladium, and (c) sintering the supported palladium at a temperature in the range of from 650° C. to 1000° C. in the presence of a gas consisting essentially of a reducing gas, an inert gas or a mixture thereof and in which process the catalyst comprises a potassium acetate promoter at a concentration of from approximately 1.5 to 5 wt % potassium.

2. The process as claimed in claim 1 wherein the ethylene, acetic acid and oxygen-containing gas is contacted with the catalyst at a temperature in the range of 145° C. to 195° C. and a pressure of from 1 to 20 atmospheres.

3. The process as claimed in claim 1 wherein the palladium catalyst comprises at least 0.5% by weight palladium based upon the total weight of the catalyst.

4. The process as claimed in claim 3 wherein the palladium catalyst comprises up to 10% by weight based upon the total weight of the catalyst.

5. The process as claimed in claim 1 wherein the catalyst support comprises porus silica, alumina, silica/alumina, titania, zirconia or carbon.

6. The process as claimed in claim 1 wherein the palladium support is impregnated in step (a) with gold, copper and/or nickel compounds.

7. The process as claimed in claim 1 wherein the support is additionally impregnated with one or more salts of Group I, II, Lanthanide and transition metals.

8. The process as claimed is claim 1 in which step (b) is carried out by contacting the palladium compound with a liquid or gaseous reducing agent selected from the group consisting of aqueous hydrazine, formaldyhyde, sodium formate, alcohol, carbon monoxide, carbon dioxide, hydrogen and ethylene.

9. The process as claimed in claim 1 wherein in step (c) the reducing gas is selected from the group consisting of hydrogen and carbon monoxide and the inert gas is selected from the group consisting of nitrogen, carbon dioxide and helium.

10. The process as claimed in claim 1 wherein the time for the sintering step (c) is between 1 and 24 hours.

11. The process as claimed in claim 1 in which the sintering step (c) causes palladium metal particle growth from 3–4 nm in diameter to 8–15 nm in diameter.

* * * * *

UNITED STATES PATENT AND TRADEMARK OFFICE
CERTIFICATE OF CORRECTION

PATENT NO.      : 6,407,283 B2                                                          Page 1 of 1
DATED           : June 18, 2002
INVENTOR(S)     : John William Couves et al.

It is certified that error appears in the above-identified patent and that said Letters Patent is hereby corrected as shown below:

<u>Title page,</u>
Item [30], insert as follows:

-- [30] Foreign Application Priority Data

Nov. 4, 1996    [GB]           United Kingdom...........9622991 --

Signed and Sealed this

Fifth Day of November, 2002

Attest:

Attesting Officer

JAMES E. ROGAN
*Director of the United States Patent and Trademark Office*